United States Patent [19]
White

[11] Patent Number: 4,661,109
[45] Date of Patent: Apr. 28, 1987

[54] INTRAOCULAR LENS

[76] Inventor: Thomas C. White, 1701 S. Minnesota Ave., Sioux Falls, S. Dak. 57105

[21] Appl. No.: 766,732

[22] Filed: Aug. 16, 1985

[51] Int. Cl.⁴ ............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 4,244,060 | 1/1981 | Hoffer | 623/6 |
| 4,495,665 | 1/1985 | Kelman | 623/6 |
| 4,562,600 | 1/1986 | Ginsberg et al. | 623/6 |

OTHER PUBLICATIONS

Medical Optics PC-15L Posterior Chamber Intraocular Lens (advertisement), Oct. 1983.

*Primary Examiner*—Ronald L. Frinks
*Attorney, Agent, or Firm*—Gregory P. Kaihoi; James R. Haller

[57] ABSTRACT

An intraocular lens for replacing the natural human eye lens during cataract surgery. The lens provides fixation struts for centering the lens within the eye, and is characterized by including posteriorly extending protrusions on portions of the struts. The protrusions define generally a plane spaced posteriorly of the lens body, and thereby hold the intact posterior lens capsule away from the lens body, facilitating the performance of a posterior capsulotomy using a laser beam. The protrusion desirably is carried on the portion of the strut adjacent the lens body, and preferably extends about the circumference of the lens at least about 45 degrees of the periphery of the lens at a distance closer to the lens periphery than about one-half of the radial distance from the lens periphery to the tissue-engaging surface of the strut.

8 Claims, 14 Drawing Figures

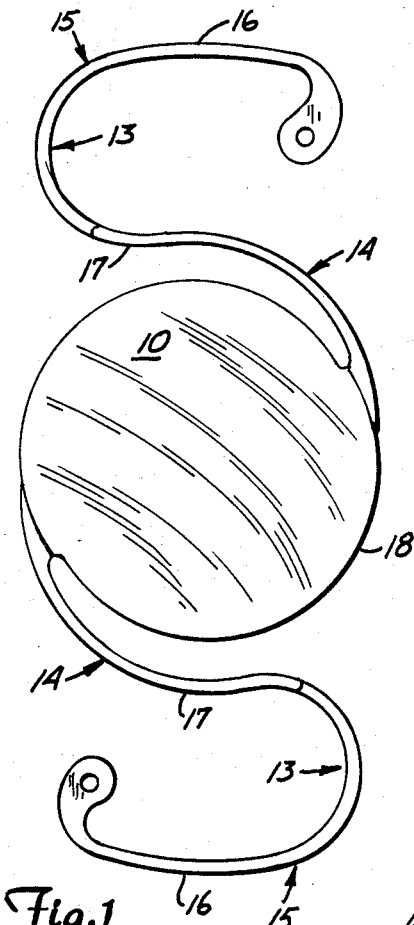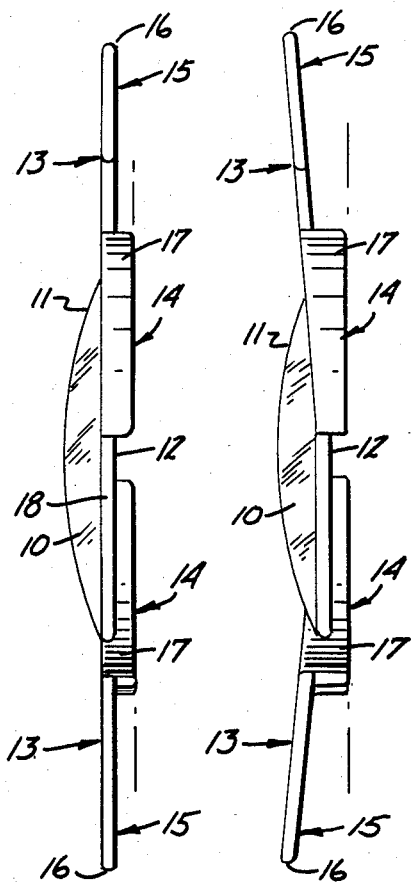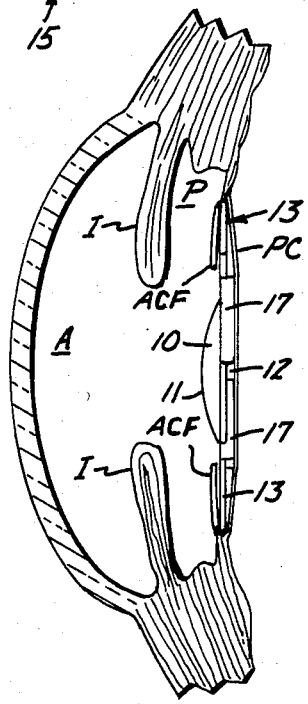
Fig.1  Fig.2  Fig.4  Fig.3

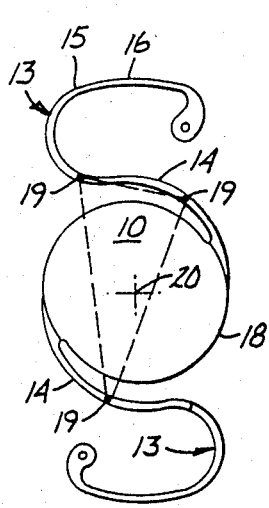
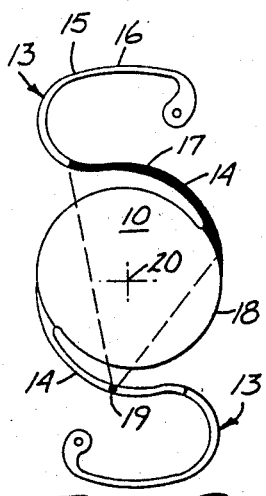
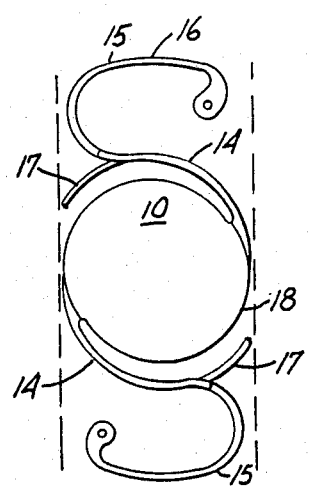
Fig. 11A  Fig. 11B  Fig. 8
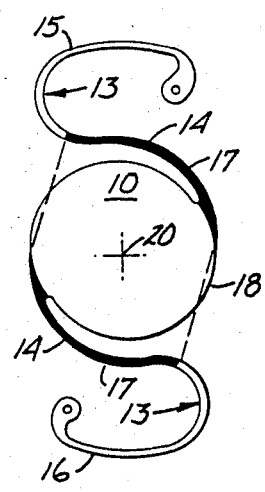
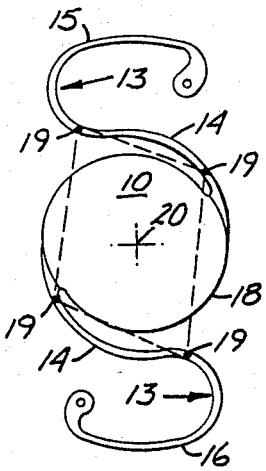
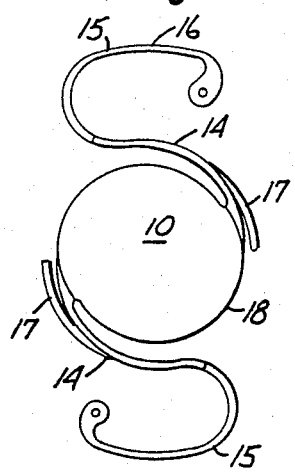
Fig. 11C  Fig. 11D  Fig. 9
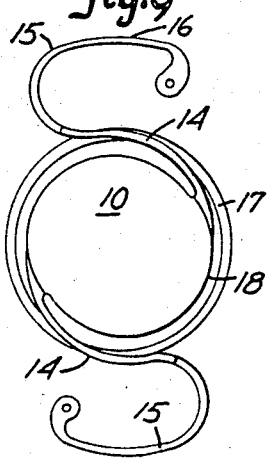
Fig. 10

INTRAOCULAR LENS

TECHNICAL FIELD

This invention is in the field of medical prosthesis, and particularly relates to the use of artificial lenses to replace tissue lenses removed during cataract surgery.

BACKGROUND ART

Extracapsular cataract extraction involves the removal of the lens nucleus from the eye of a patient. Commonly an incision is made in the anterior capsule, and the clouded lens tissue contained within the capsule is removed; the posterior capsule and peripheral portions of the anterior capsule (the "anterior capsule flaps") are left intact. An artificial intraocular lens may then be implanted in the eye, the lens being supported in either the anterior or posterior chamber and being positioned by wires or other structure that extend from the lens outwardly into contact with supportive, circumferential tissue adjacent the iris.

Typical intraocular lenses are disclosed in the following references:

U.S. Pat. No. 4,092,743 (Kelman);
U.S. Pat. No. 4,174,543 (Kelman);
U.S. Pat. No. 4,244,060 (Hoffer);
U.S. Pat. No. 4,261,065 (Tennant);
U.S. Pat. No. 4,328,595 (Sheets);
U.S. Pat. No. 4,338,687 (Rainin);
U.S. Pat. No. 4,340,979 (Kelman);
U.S. Pat. No. 4,343,050 (Kelman);
U.S. Pat. No. 4,370,760 (Kelman);
U.S. Pat. No. 4,412,359 (Myers).

Intraocular lenses in general are characterized by including a central lens or lenticular portion, and two or more struts, usually radially resilient, that extend outwardly of the lens and which gently but elastically engage appropriate circumferential eye structure adjacent the iris. The struts of intraocular lenses that are to be employed in the anterior chamber of the eye commonly are supported in the angle formed between the iris and the internal periphery of the cornea, avoiding substantial contact or interference with the trabacular meshwork. Intraocular lenses intended to be mounted in the posterior chamber commonly have struts or other fixation devices that engage the ciliary recess or the periphery of the posterior lens capsule that remains after removal of the lens nucleus.

Occasionally after cataract surgery and placement of an intraocular lens within the eye, it becomes necessary to perform a posterior capsulotomy to alleviate cloudiness of the posterior capsule which frequently develops over time after cataract surgery. Such cloudiness is generally due to the growth of lens fibers or capsular fibrosis. Some recent studies have indicated that the growth of lens fibers or capsular fibrosis may be caused by cells on the intact anterior capsule flaps migrating toward and/or contacting the posterior capsule. Historically, the cloudiness was removed by performing a discission; a small knife was inserted behind the intraocular lens and used, under a microscope, to trim away the clouded portion of the posterior capsule.

With the development of modern laser technology it is now possible to perform a posterior capsulotomy without surgically entering the eye by use of a laser beam focused upon the posterior capsule. A number of small holes are made in the capsule in a number of locations until the center portion has been removed, providing a clear "window" for unobstructed light to pass through the lens rearwardly to the retina. A popular laser for use in this technique is the "YAG" laser (Yttrium-aluminum-garnet).

If the intraocular lens is mounted in the posterior lens capsule, however, the lens commonly lies in face-to-face contact with the anterior surface of the posterior capsule. When a laser is focused on the posterior capsule, local intense heating occurs which may shatter or otherwise damage the lens.

One solution which has been offered to alleviate this problem is to include a posteriorly projecting ring on the posterior surface of the intraocular lens body to space the posterior capsule of the eye from the confronting lens surface. Such rings are disclosed in U.S. Pat. Nos. 4,244,060 (Hoffer), and 4,412,359 (Myers).

Such rings on the lens body have at least two disadvantages, however. First, they are optical aberrations on the lens, not only diffusing the light rays passing through the lens, but also causing distracting reflections of light within the eye. These problems are particularly acute when the iris is dilated, and may be exasercabted if the lens is not perfectly centered. Secondly, depending upon the physical dimensions, placement, and orientation of the lens, such rings may inhibit the ability of a physician to properly examine peripheral portions of the retina. Such examinations are important to the diagnosis of various eye disorders including retinal detachments, retinal holes or tears, tumors, cysts, and so forth.

DISCLOSURE OF INVENTION

The invention provides an intraocular lens for placement adjacent to the anterior surface of the posterior capsule of an eye. The lens includes a lens body having a central axis and anterior and posterior surfaces. The lens also includes posteriorly extending protrusion means spaced generally radially outwardly of the lens body beyond its periphery for contact with the posterior lens capsule to space the posterior surface of the lens from the posterior capsule by a distance of at least about 0.1 mm. Means is also provided to connect the protrusion means to the lens body.

Desirably the connecting means includes strut means carried by the lens body and extending generally radially outwardly for contact with peripheral eye tissue to secure the lens in the posterior chamber of the eye adjacent to the posterior capsule. Preferably the strut means includes at least two elongated, resilient struts, each strut being carried at a first end by the lens body and having a first portion carrying the protrusion means and extending outwardly of the lens generally toward circumferential eye tissue, and a second portion having an outwardly facing, tissue-engaging surface for supportive engagement with peripheral eye tissue. The first portion, for at least about 45 degrees of the circumference of the lens, preferably is spaced from the periphery of the lens body by a distance less than about one-half of the radial distance from the lens body periphery to the tissue-engaging surface.

The protrusion means preferably includes a continuous ridge along the first portion of each strut, the ridge extending posteriorly of the posterior-most portion of lens body by a distance of about 0.1 mm to 1.0 mm. Alternately, the protrusion means may comprise any of a variety of configurations so constructed and arranged as to provide at least three spaced points of contact with the posterior capsule, said points of contact defining a closed curve through which the lens axis passes. The protrusion means may also be configured and arranged to space the anterior capsule flaps from the posterior capsule.

BRIEF DESCRIPTION OF DRAWINGS

FIG. 1 is a plan view of an intraocular lens of the invention;

FIG. 2 is a side view of the intraocular lens of FIG. 1;

FIG. 3 is a cross-sectional broken-away view of the human eye, shown somewhat schematically, depicting implantation of the lens of the lens of the invention in the posterior chamber;

FIG. 4 is a side view of a modified embodiment of the invention similar to FIG. 2;

FIG. 8 is an anterior plan view of a modified embodiment of the invention;

FIG. 9 is an anterior plan view of another modified embodiment of the invention;

FIG. 10 is an anterior plan view of another modified embodiment of the invention; and FIGS. 11A–D are plan views of various modified embodiments of the invention.

BEST MODE FOR CARRYING OUT THE INVENTION

Figure 5:
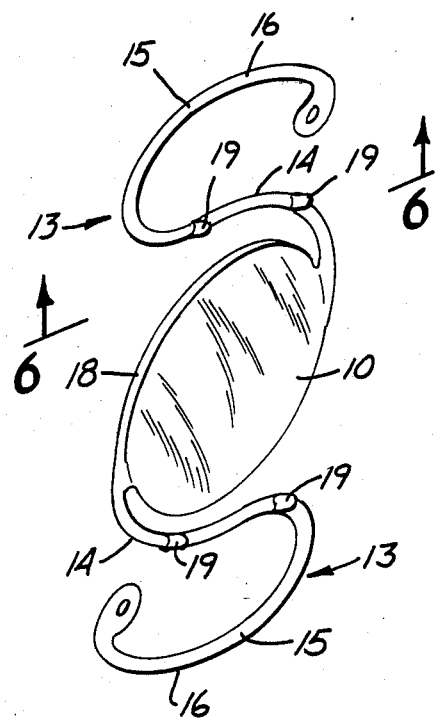
FIG. 5 is a perspective posterior view of a modified embodiment of the invention.

FIG. 1 shows a lens of the invention which may be made from polymethyl methacrylate or other suitable transparent, implantable material. The lens includes an optical body (10) having anterior (11) and posterior (12) surfaces, and fixation struts (13) extending generally radially outwardly from the lens body (10) for contact with peripheral eye tissue to secure the lens in the posterior chamber of the eye. Although a preferred strut (13) is shown in the drawings, subject to the parameters set forth herein any of a variety of strut configurations may be used.

Each fixation strut (13) includes a first portion (14) extending outwardly of the lens generally toward circumferential eye tissue, and a second portion (15) having an outwardly facing, tissue-engaging surface (16) for supportive engagement with peripheral eye tissue. The first portion (14) desirably carries protrusion means for contact with the posterior capsule of the eye. Protrusion means might be carried by separate connecting means independent of the struts (13), but use of the struts (13) to carry the protrusion means is particularly desirable.

FIG. 2 shows the preferred protrusion means which comprises a ridge (17) extending posteriorly from the first portion (14) of the strut (13). The ridge (17) desirably extends posteriorly of the posterior-most portion of the lens body (10) by a sufficient distance (e.g., about 0.1 mm to 1.0 mm) to space the posterior capsule (PC) of the eye from the posterior surface (12) of the lens body (10). The lens shown in FIG. 2 is plano-convex in configuration; if a bi-convex lens body is desired, the ridge (17) of the invention should extend a distance of about 0.1 mm–1.0 mm posteriorly of the posterior-most portion of the bi-convex lens body. The struts (13) in FIG. 2 extend substantially co-planarly from the lens body (10); FIG. 4 shows a modified embodiment wherein the struts (13) extend angularly anteriorly, thereby vaulting the lens body (10) posteriorly.

Figure 6:
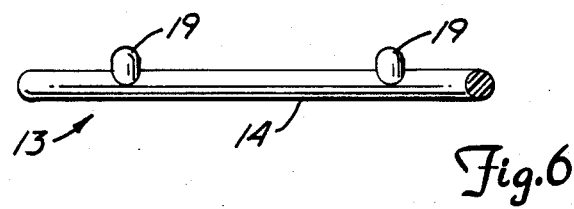
FIG. 6 is a cross-sectional view taken along line 6—6 of FIG. 5.
Figure 7:
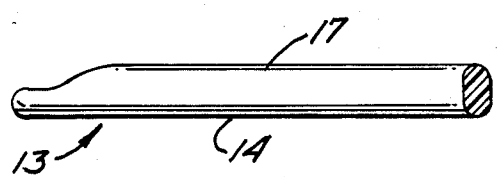
FIG. 7 is a view similar to FIG. 6 showing a modified embodiment thereof.

Desirably, the protrusion means is carried on the first portion (14) of the strut (13), said first portion (14) being spaced generally radially from the periphery (18) of lens body (10) by a distance less than about one-half of the radial distance from the lens body periphery (18) to the tissue-engaging surface (16) of the second portion (15) of the strut (13). In a preferred embodiment, as shown in FIGS. 1–4 and 7, the ridge (17) is continuous along the first portion (14) of each strut (13); said first portion (14), for an arc of at least about 45 degrees of the circumference of the lens body (10), is spaced radially from the periphery (18) of the lens body (10) by a distance less than about one-half of the radial distance from the lens body periphery (18) to the tissue-engaging surface (16). In another embodiment, shown in FIGS. 5–6, the protrusion means comprises a plurality of knobs (19) carried by the first portions (14) of the struts (13).

The efficacy of the protrusion means in spacing the posterior capsule (PC) from the lens body (10) is related to the size and positioning of the protrusion means. Although the protrusion means need not be entirely coplanar, preferably it defines generally a plane spaced posteriorly of the posterior-most portion of the lens body (10). This plane may be defined by three or more points of contact, by a point and a line segment, or by multiple line segments.

Preferably the protrusion means includes a plurality of points of contact so configured and arranged as to define a closed curve through which the lens axis (20) passes. As used herein, the phrase "points of contact" is to be understood in its technical geometric sense; thus a line or arcuate segment is comprised of an infinite number of adjacent points. Because the protrusion means is not necessarily planar, technically it is the projection of the protrusion means, onto a plane normal to the axis of the lens, which defines the closed curve. Protrusion means meeting the above stated criterion may be said to be "balanced".

FIG. 11 shows, by way of example, four possible "balanced" configurations. In FIG. 11A, the protrusion means comprises three knobs (19) which provide three spaced points of contact. The knobs (19) define a triangle (indicated by broken lines) through which the lens axis (20) passes. The protrusion means in FIG. 11B includes a knob (19) carried on one strut (13) and a ridge (17) (indicated in black shading) carrried by the other strut (13), the knob (19) and ridge (17) defining a closed curve through which the lens axis (20) passes. Similarly, the protrusion means of FIGS. 11C and 11D include respectively two ridges (17) and four knobs (19), defining respectively closed curves through which the respective axes (20) pass.

The significance of requiring the protrusion means to be "balanced" (as defined above) relates to positioning of the lens within the capsule. If the protrusion means is not "balanced," when implanted the lens may become skewed with respect to the optical axis (20) of the eye, just as a three-legged table would tip over unless the projection of its center of gravity onto the floor lies with the triangle defined by the table legs. Preferably the protrusion means includes at least one continuous ridge (17), such as is shown in FIGS. 1–4, having an arc of at least about 45° of the circumference of the lens.

FIG. 3 depicts a lens of the invention which has been surgically placed within the lens capsule. In this figure, the iris is designated as "I", the anterior chamber as "A", the posterior chamber as "P", the posterior capsule as "PC", and the anterior capsule flaps as "ACF". As can be seen from this figure, the ridge (17) does not inhibit a physician's ability to examine the peripheral portions of the retina; nor does the ridge (17) interfere in any way with the proper passage of light rays through the lens body (10), eliminating the possibility of optical reflections and diffusion.

FIG. 3 also depicts cooperation of the struts (13) and ridges (17) to space the anterior capsule flaps (ACF) from the posterior capsule (PC) to inhibit cellular contact with and/or migration toward the posterior capsule (PC), thereby inhibiting growth of lens fibers or capsular fibrosis which causes clouding of the posterior capsule. The spacing of the anterior capsule flaps (ACF) from the posterior capsule (PC) may be enhanced by extending the protrusion means circumferentially about the lens body (10). FIGS. 8–10 show, in anterior plan view, three such modified embodiments. FIGS. 8 and 9 include partial circumferential ridges (17), and FIG. 10 shows an unbroken circumferential ridge (17). Preferably the protrusion means extends for at least about 180° (in the aggregate) about the periphery (18) of the lens body (10). The configurations shown also enhance spacing of the posterior capsule (PC) from the posterior surface (12) of the lens body (10). The embodiment of FIG. 8 is particularly desirable because the protrusion means does not increase the overall width of the device, and therefore does not affect the minimum size of incision or iris diameter through which the lens will pass.

The lens of the invention may be manufactured from any appropriate material, but preferably is made of an optically clear plastic such as polymethyl methacrylate. Molding and lathe cutting of such lenses are well known in the art, and need not be described in detail. The protrusion means may be integrally molded with the lens strut (13), or may be affixed to the strut (13) after manufacture of the latter, as by adhesive bonding, for example.

In use, a lens of the invention is surgically implanted within the capsule of the eye by well known surgical techniques, following removal of the natural lens nucleus and the central portion of the anterior capsule. The protrusion means, depending upon its configuration, may assist in preventing lens fiber growth or capsular fibrosis by spacing the anterior capsule flaps (ACF) from the posterior capsule (PC), thereby inhibiting cellular contact with and/or migration toward the posterior capsule (PC). After passage of time, if the posterior capsule (PC) has clouded and must be removed, a posterior capsulotomy may be performed by focusing an appropriate laser beam (such as the YAG laser) on the posterior capsule (PC), thereby forming holes in the capsule (PC) until the appropriate portion has been removed. Although the posterior capsule (PC) would normally be in face-to-face contact with the posterior surface (12) of the lens body (10), the protrusion means spaces the capsule (PC) away from the lens body (10), providing sufficient thermal isolation to prevent damage to the lens body (10) from the local intense heating of the posterior capsule (PC).

While a preferred embodiment of the present invention has been described, it should be understood that various changes, adaptations, and modifications may be made therein without departing from the spirit of the invention and the scope of the appended claims.

What is claimed is:

1. An intraocular lens for placement adjacent to the anterior surface of the posterior lens capsule of an eye, comprising: a lens body having a central axis, an anterior surface, and a posterior surface; posteriorly extending protrusion means spaced generally radially outwardly from the lens body for contact with the posterior capsule to space the posterior surface of the lens body from the posterior capsule by a distance of at least about 0.1 mm; and strut means carried by the lens body and extending generally radially outwardly for contact with peripheral eye tissue to secure the lens in the posterior chamber of the eye adjacent to the posterior capsule, the strut means including:
   one or more elongated, resilient struts, each said strut being carried at a first end by the lens body and having a first portion carrying the protrusion means and extending outwardly of the lens generally toward circumferential eye tissue, said first portion, for at least about 45 degrees of the circumference of the lens, being spaced radially from the periphery of the lens body by a distance less than about one-half of the radial distance from the lens body periphery to the tissue-engaging surface; and
   a second portion having an outwardly facing, tissue-engaging surface for supportive engagement with peripheral eye tissue.

2. The lens of claim 1 wherein the protrusion means includes a continuous ridge along said first portion of at least one of the struts, said ridge extending posteriorly of the posterior-most portion of the lens body by a distance of at least about 0.1 mm.

3. The lens of claim 1 wherein the protrusion means is so constructed and arranged as to provide at least three spaced points of contact with the posterior capsule sufficient to prevent contact of the posterior capsule with the posterior surface of the lens.

4. The lens of claim 3 wherein the points of contact define a closed curve through which the lens body axis passes.

5. The lens of claim 1 wherein the protrusion means extends for at least about 180° of the periphery of the lens body.

6. The lens of claim 1 wherein the protrusion means extends for 360° about the periphery of the lens body.

7. An intraocular lens for placement adjacent to the anterior surface of the posterior capsule of an eye, comprising:
   (a) a lens body having an anterior surface, a posterior surface, and a central axis; and strut means carried by the lens body and extending peripherally therefrom for contact with peripheral eye tissue to secure the lens in the posterior chamber of the eye adjacent to the posterior capsule, the strut means including two elongated, resilient struts, each strut being carried at a first end by the lens and having a first portion extending outwardly of the lens generally toward circumferential eye tissue, and a second portion having an outwardly facing, tissue-engaging surface for supportive engagement with peripheral eye tissue, the first portion, for at least about 45 degrees of the circumference of the lens, being spaced radially from the periphery of the lens body by a distance less than about one-half of the radial distance from the lens body periphery to the tissue-engaging surface; and
   (b) posteriorly extending protrusion means carred by the first portion of each strut for contact with the posterior capsule to space the posterior surface of the lens body from the posterior capsule by a distance of at least about 0.1 mm, the protrusion means being so constructed and arranged as to provide at least three spaced points of contact with the posterior capsule sufficient to prevent contact of the posterior capsule with the posterior surface of the lens, the points of contact defining a closed curve through which the lens axis passes.

3. The lens of claim 7 wherein the protrusion means includes a continuous ridge along the first portion of each strut, said ridge extending posteriorly of the posterior-most portion of the lens body by a distance of at least about 0.1 mm.

* * * * *